United States Patent
Gärber et al.

(10) Patent No.: US 9,872,632 B2
(45) Date of Patent: Jan. 23, 2018

(54) ELECTRIC IMPEDANCE TOMOGRAPHY DEVICE AND METHOD

(71) Applicant: Dräger Medical GmbH, Lübeck (DE)

(72) Inventors: Yvo Gärber, Breitenfelde (DE); Ola Stenqvist, Viken (SE)

(73) Assignee: Draegerwerk AG & Co. KGaA, Lübeck (DE)

( * ) Notice: Subject to any disclaimer, the term of this patent is extended or adjusted under 35 U.S.C. 154(b) by 668 days.

(21) Appl. No.: 14/172,254

(22) Filed: Feb. 4, 2014

(65) Prior Publication Data
US 2014/0221865 A1 Aug. 7, 2014

(30) Foreign Application Priority Data

Feb. 5, 2013 (DE) .................. 10 2013 201 804
Jul. 10, 2013 (DE) .................. 10 2013 213 526

(51) Int. Cl.
| | |
|---|---|
| A61B 5/08 | (2006.01) |
| A61B 5/053 | (2006.01) |
| A61B 5/00 | (2006.01) |
| A61B 5/087 | (2006.01) |

(52) U.S. Cl.
CPC ........... *A61B 5/0536* (2013.01); *A61B 5/087* (2013.01); *A61B 5/0809* (2013.01); *A61B 5/6823* (2013.01); *A61B 5/7239* (2013.01)

(58) Field of Classification Search
CPC ..... A61B 5/0536; A61B 5/087; A61B 5/6823; A61B 5/7239; A61B 5/0809
See application file for complete search history.

(56) References Cited

U.S. PATENT DOCUMENTS

| | | | |
|---|---|---|---|
| 8,321,007 B2 | 11/2012 | Teschner et al. | |
| 2010/0228143 A1* | 9/2010 | Teschner | A61M 16/0051 600/547 |

FOREIGN PATENT DOCUMENTS

| | | |
|---|---|---|
| EP | 1 000 580 A1 | 5/2000 |
| EP | 2 228 009 A1 | 9/2010 |

OTHER PUBLICATIONS

Costa, et al. "Real-time detection of pneumothorax using electrical impedance tomography." Critical Care Medicine, vol. 36, No. 4. 2008 pp. 1230-1238.*

(Continued)

*Primary Examiner* — Tiffany Weston
(74) *Attorney, Agent, or Firm* — McGlew and Tuttle, P.C.

(57) ABSTRACT

An electric impedance tomography device with chest electrodes, a display and a control and analyzing unit to determine a time series of a global ventilation curve from the sequence of reconstructed matrices as a time series of the mean impedance change or of a measured respiration volume, to divide an inspiration or expiration phase into a number of steps of equal volume change, to determine the times corresponding to these steps, to determine the change in local impedance between these times for each image element, the ratio of this local change in impedance to the global ventilation curve to form a local sequence of relative impedance changes of the image element as a function of the steps of equal volume change, to determine a scalar indicator characteristic as a function of the steps of equal volume change and to display each image element based on the respective scalar indicator.

17 Claims, 4 Drawing Sheets

(56) References Cited

OTHER PUBLICATIONS

Lowhagen et al., Regional intratidal gas distribution in acute lung injury and acute respiratory distress syndrome-assessed by electric impedance tomography, Minerva Anestesiologica, Dec. 2010, pp. 1024-1035, vol. 76—No. 12.

* cited by examiner

ELECTRIC IMPEDANCE TOMOGRAPHY DEVICE AND METHOD

CROSS REFERENCE TO RELATED APPLICATIONS

This application claims the benefit of priority under 35 U.S.C. §119 of German Patent Application DE 10 2013 201 804.5 filed Feb. 5, 2013 and German Patent Application DE 10 2013 213 526.2 filed Jul. 10, 2013, the entire contents of each are incorporated herein by reference.

FIELD OF THE INVENTION

The present invention pertains to an electric impedance tomography device with a plurality of electrodes that can be arranged about the chest of a patient, with a control and analyzing unit, which is set up by programming (configured) to supply at least one electrode pair as a feeding electrode pair with an alternating current or with an alternating voltage, to record a voltage signal or current signal as a measured signal with a plurality of the other electrode pairs, and to let each electrode pair of the plurality of electrode pairs act consecutively as the feeding electrode pair in order to reconstruct from the measured signals with a reconstruction algorithm a matrix of image elements, which represents the distribution of the impendence changes in the electrode plane and to repeatedly record measured signals over one breath and to reconstruct matrices.

BACKGROUND OF THE INVENTION

Such an electric impedance tomography device (EIT device) is known, for example, from EP 1 000 580 A1, which is used to record an "electric impedance tomogram" of a chest cross section of a patient.

Electric impedance tomography is a method for the reconstruction of impedance distributions, more precisely, of impedance changes relative to a reference distribution, in electrically conductive bodies. A plurality of electrodes are arranged for this purpose on the surface of the body to be examined. A ring-shaped, equidistant array of 16 electrodes, which can be laid around the chest of a patient with a belt, is used in typical cases. The control and analyzing unit also has analog electric circuits for signal amplification and for feeding alternating current and electronic circuits for digitizing and preprocessing the voltage signals as well as a digital signal processor for controlling the device and for processing the recorded data to reconstruct the impedance distribution. The control and analyzing unit ensures that a pair (preferably) of adjacent electrodes are consecutively supplied with an electric alternating current (e.g., 5 mA at 50 kHz) and the electric voltages are detected at the remaining electrodes by the control and analyzing unit (it is also possible, conversely, to feed an alternating voltage to one electrode pair and to measure the alternating currents over a plurality of remaining electrode pairs); the voltages of all remaining pairs of adjacent electrodes are typically detected, but it is also possible, in principle, to omit individual electrodes, as a result of which information is, however, lost. The impedance change, more precisely, the impedance change relative to a reference distribution (e.g., the impedance distribution during the first recording) can be reconstructed with algorithms from the totality of all measured signals during the consecutive current feeds, during which the position of the feeding electrode pair migrates step by step about the electrode ring. The impedance distribution, more precisely the change in impedance relative to a reference distribution (e.g., the impedance distribution during the first recording) can be reconstructed with algorithms from all the measured signals during the consecutive current feeds, during which the position of the feeding electrode pair migrates step by step around the electrode ring. The prior-art algorithms furnish as the reconstruction result a matrix of 32×32 image elements, wherein the matrix contains for each image element the reconstructed impedance change for that image element. A plurality of such matrices are recorded during each breath at preset time intervals. These are displayed consecutively on a display, as a result of which the intratidal changes in impedance distribution over time are made visible practically as a film (movie).

Electric impedance tomography of the chest for measuring the regional lung ventilation has been increasingly used in research-focused intensive care. Theoretical models and experimental comparisons of EIT with CT images of the chest show a nearly complete proportionality of the air content in the lung tissue to the impedance thereof. The breaths are resolved in space with about 20% of the chest diameter and in time typically with about 20 to about 40 matrices per second, which makes bedside monitoring of the regional lung ventilation possible. The matrices are occasionally also called images of the impedance distribution (with 32×32=1024 image elements) or frames.

Consequently, a sequence of impedance changes, which is also called time series of impedance change values for the given image element, is determined for each image element over one phase of inspiration or expiration. The terms "impedance change values and impedance change curves" will be used synonymously below, even though a time series consisting of discrete points is not a curve in the strict sense of the word. The time series are also represented in the form of curves as functions of time in the views for reasons of representation.

One essential advantage of the high frame rate is that the breaths, especially their inspiration and expiration phases, can be resolved in time. It is therefore possible to only analyze the regional distribution of the ventilated air in the end-inspiratory status (tidal image), but also to investigate the changes over time during the inspiration and expiration in order to infer regional lung mechanical processes therefrom. For example, local inspiration curves are determined, for example, in the article "Regional ventilation delay index: Detection of tidal recruitment using electric impedance tomography," T. Muders et al., Vincent J. L., Editor, Yearbook of Intensive Care and Emergency Medicine, and the time at which it has reached 40% of its maximum, is related for each local inspiration curve with the global inspiration time and an image or faster or slower regions with lower or higher time constants than the average is generated therefrom. A "regional ventilation delay index (RVD)" is defined from this as an indicator of the inhomogeneity over time.

One more step is taken in EP 2 228 009 A1 and the global inspiration or expiration phase is divided into a plurality of equidistant volume steps and the intratidal variations (ITV), i.e., the redistribution of the ventilated partial volumes per volume step, into so-called "regions of interest" (ROI), which comprise a defined number of image elements, is determined. The result is then shown in curves specific of the ROIs over equidistant volume steps or variables coupled therewith. It is thus determined which lung areas contain more or less air than the other areas at which time during inspiration or expiration. In the ideal case, which is homogeneous over time, everything remains constant. By contrast, there are redistributions in lungs that are inhomogeneous over time. The advantage of the greater division of the respiration flanks of the ITV compared to the viewing of the one, 40% threshold value in RVD is that curves are viewed over ROIs that are coarser in space and, unlike in RVD, curves rather than an image that would be visually accessible in a simple manner are available. Moreover, inhomogeneities over time may possibly be overlooked due to unfavorable selection of the ROIs. Furthermore, no global ITV parameter analogous to the RVD index, which would show upon first glance whether redistributions are present, is defined.

SUMMARY OF THE INVENTION

An object of the present invention is to provide an electric impedance tomography device and a corresponding method and system with which intratidal redistributions can be locally detected and a redistribution indicator coded as an image can be displayed to make possible the rapid visual detectability of the local intratidal redistributions.

According to the invention, an electric impedance tomography device is provided with a plurality of electrodes, which can be arranged about the chest of a patient with a control and analyzing unit and a display device. The control and analyzing unit is set up by programming (configured) to supply an electrode pair as a feeding electrode pair with an alternating current or with an alternating voltage, to record a voltage signal or current signal as measured signal from each electrode pair of all other electrode pairs, and to let each electrode pair of the plurality of electrode pairs act consecutively as the feeding electrode pair, and to reconstruct, from the measured signals with a reconstruction algorithm, a matrix of image elements, which represents the distribution of the impedance changes in the electrode plane, and to repeatedly record measured signals over time and to reconstruct matrices. The control and analyzing unit of the EIT device is set up (configured) according to the present invention to determine a time series of the global ventilation curve from the sequence of the reconstructed matrices as a time series of the mean impedance change or as a time series of a measured respiration volume and to determine therein an inspiration phase or expiration phase. Provisions are, furthermore, made to divide the inspiration phase or expiration phase in the global ventilation curve into a number (1, 2, . . . $M_{steps}$) of steps of equal volume change and to determine the times corresponding to these steps of equal volume change in the inspiration phase or expiration phase. The control and analyzing unit is set up, furthermore, to determine the ratio of the impedance change of the image element to the global ventilation curve for each image element at the times determined in order to thus form a local sequence of the relative impedance change of the image element as a function of the steps of equal volume change. Provisions are, furthermore, made to determine, for each local sequence of the relative impedance change of the image element as a function of the steps of equal volume change, a scalar indicator characteristic of the curve of the volume change over the inspiration phase or expiration phase and to display each image element on the display means (display device) in a manner dependent on the particular scalar indicator.

The inspiration or expiration phase in the global ventilation curve is divided into a number of steps (1, 2, . . . $M_{steps}$) of equal volume change $\Delta V$, the times corresponding to these steps of equal volume change in the inspiration or expiration phase are determined, and the ratio of the local impedance change of the image element to the global ventilation curve is then determined for each image element at the times determined. This sequence of ratios is then plotted as a function of the volume change steps (1, 2, . . . $M_{steps}$) and analyzed in order to determine the scalar indicator of the local curve of ventilation in each image element over the inspiration or expiration phase. This volume change $\Delta V$ is determined practically for each step by dividing the entire volume change over the inspiration or expiration phase by the preset number of steps $M_{steps}$. For example, 8 steps are used in the exemplary embodiments. The analysis of the local time series at equal volume change steps $\Delta V$ of the global ventilation curve means practically that the local curve of the ventilation change is plotted as a function of the global ventilation curve, i.e., the x axis with the steps (1, 2, . . . $M_{steps}$) corresponds to the equidistant $\Delta V$ steps of the increasing global ventilation volume up to the total inspiration volume and the y axis corresponds to the ratio of the local variable ventilation change curve to the global ventilation change $\Delta V$.

The following terms will be hereinafter used as abbreviations:

The relative change between the steps m and m+1 of the time series of the local impedance change of an image element relative to the global volume or impedance change step $\Delta V$ and $\Delta Z_{glo}$ for one of the m=1, 2, . . . , $M_{steps}$ steps is called the m-th local ITV value of the image element (ITV: Intratidal distribution).

The value pairs (m=1, first ITV value) . . . (m=$M_{steps}$, $M_{steps}$, $M_{steps}$-th ITV value) of all local ITV values, which value pairs are ordered from m=1 to $M_{steps}$, are called local ITV curve of the image element. The ITV curves are thus a function of the ITV values as a function of the m=1 . . . $M_{steps}$ steps.

The scalar indicator of the local ITV curve of an image element is also called local ITU value of the image element (ITU: Intratidal redistribution).

In an advantageous embodiment, the control and analyzing unit is set up to determine as the scalar indicator of the ITV curves of the inspiration or expiration phase the mean slope thereof, possibly multiplied by the number of steps $M_{steps}$, maxima of the local ITV values within the inspiration or expiration phase or the maximum change in the local ITV values within the inspiration or expiration phase or zero positions. It is easy to see that, for example, the mean slope or the standard deviation of the ITV curves over the inspiration or expiration phase provide essential information on the changes in ventilation over time in the local lung elements. Maxima of the ITV values within the inspiration or expiration phase contain information on whether there are any jumps over the time curve in the ventilation curve, which jumps are manifest in the value after high (positive or negative) local slopes in the area of a jump. The maximum change of the ITV values within the inspiration or expiration phase contains information on whether any sudden, very great changes occur in the local ventilation curve. Zero positions of the interpolated ITV curve in the area of the tidal stroke between expiration and inspiration may be indicative of tidal recruitment hyperdistension.

The control and analyzing unit is setup, furthermore, in a preferred embodiment to fit a straight line to the ITV curves in an inspiration or expiration phase for each image element and to also determine the zero position thereof, besides the slope thereof, to assign to this zero position a time within the inspiration or expiration phase, to assign to this time a ventilation variable, and to display the image element as a function of the ventilation variable thus determined by gray scale value or color coding on the display means. The consideration behind this procedure is that if the local impedance change curve is plotted as a function of the step number of equal global impedance or volume change steps, plotting is performed, as it were, as a function of the global impedance curve of 0, $\Delta Z_{glo}$, $2 \cdot \Delta Z_{glo}$ ... $M_{steps} \cdot \Delta Z_{glo}$ or of the global volume curve. The local ventilation curve ideally behaves in exactly the same way as the global one and a straight line in parallel to the x axis is obtained, which means that there are no differences in the course over time of the local ventilation and global ventilation: In brief, it is homogeneous over time. This plotting as a function of the global ventilation curve practically means a differentiation of the local curve according to the ventilated global volume. By looking up the zero position, practically an extreme value is detected in the local impedance curve as a function of the volume. Since the ventilated volume increases monotonically with the time during the inspiration phase and drops monotonically during the expiration phase in case of typical ventilation, this extreme in the volume likewise corresponds to one over time. In case of a positive rise of the fitted straight line during the inspiration phase, this extreme value corresponds to a minimum and therefore to the time at which the alveoli begin to open, and, during the expiration phase, to the time at which the alveoli close. The control and analyzing unit preferably links with this time a ventilation variable, e.g., the global time series of the impedance change or another determined time series of the respiration pressure, of the volume, of the flow or of the alveolar pressure determined from them with a lung mechanical model. If an image is displayed in which each image element is displayed in a corresponding coding (color coding or gray scale value coding) as a function of the ventilation variable at which the alveoli open or close, this can provide for the physician or the staff important information on how to set the respirator, for example, on what PEEP value is to be set.

The control and analyzing unit is set up, furthermore, in a preferred embodiment to display each image element as a function of the local impedance change of the image element by gray scale value or color coding on the display means for the determined times of equal volume change steps of each image element as a function of the local impedance change of the image element. Consequently, the cumulative distribution of ventilation is displayed here in a plurality of steps after an equal volume change each time over the inspiration or expiration phase. If, for example, eight steps of equal volume change are selected over the inspiration or expiration phase, eight images are generated with the local impedance changes from the beginning of inspiration until the end of inspiration or from the beginning of expiration until the end of expiration as a sequence of EIT images.

In an alternative embodiment, the control and analyzing unit is set up to display each image element as a function of the difference between the local impedance change and the impedance change at the preceding time by gray scale value or color coding on the display means starting from the second of the number of times determined for the determined times of equal volume change steps. This will then yield a sequence of differential EIT images, called intratidal distribution images, i.e., the change in the cumulative ventilation distribution relative to the preceding step for each image element.

The control and analyzing unit is set up, furthermore, in a preferred embodiment to perform the reconstruction of the matrices, the determination of the time series, of the ITV curves and of the ITU values (scalar indicators) for each image element in real time. As an alternative, the control and analyzing unit is set up to store the measured signals and to perform the reconstruction of the matrices, the determination of the time series for the global ventilation curve and the determination of the local time series, of the ITV curves and of the ITU values for each image element with a time delay or to perform the reconstruction of the matrices in real time and to store these, and the determination of the time series, of the ITV curves and of the ITU values with a time delay.

In a preferred embodiment, the control and analyzing unit is set up, furthermore, to convert the ITU values into a color code and to display the image elements in a color-coded form on the display means.

In a preferred embodiment, the control and analyzing unit is set up to combine the ITU values in the image elements into a global parameter and to display them alphanumerically and/or graphically on the display means. If the mean slope, possibly multiplied by the number of steps $M_{steps}$, is used as the ITU value of an image element, the sum over all positive or negative rises, possibly multiplied by the number of steps $M_{steps}$, or the halved sum over the values of the slopes, possibly multiplied by the number of steps $M_{steps}$, may be used as the global parameter. In the case in which the standard deviation is used as the ITU value of an image element, the standard deviation added up over all image elements or the averaged standard deviation may be used as the global parameter. If the maxima of the values of the local slopes, possibly multiplied by the number of steps $M_{steps}$, are used as the local ITU value, the sum over all maxima of the values of the local slopes, possibly multiplied by the number of steps $M_{steps}$, may be used. If the maximum slope change within the inspiration or expiration phase is used as the ITU value, the sum over all maximum slope changes, possibly multiplied by the number of steps $M_{steps}$, may be used as the global parameter.

The present invention will be described below on the basis of exemplary embodiments shown in the drawings The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
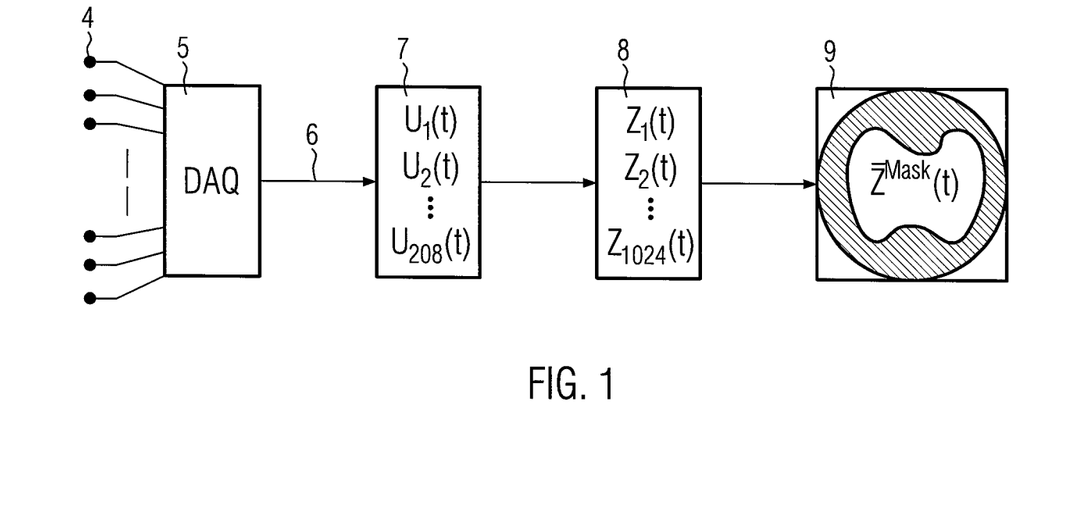
FIG. 1 is a schematic view of components or modules of the electric impedance tomography device for explaining the functions thereof.

Referring to the drawings in particular, a 16-electrode system is used in this example in the detail from the EIT device shown in FIG. 1, wherein the electrodes 4 are arranged in a ring-shaped pattern about the chest. Current feed takes place via a pair of (preferably) adjacent electrodes, voltage measurements are performed via a plurality of the remaining adjacent electrode pairs, and current feed is then performed via another pair of adjacent electrodes, etc., by means of the data acquisition unit 5 of the EIT device until a plurality of or all adjacent electrode pairs will have acted once as a feeding electrode pair; the measured voltages thus obtained are also called frames. One frame of measured voltages comprises 208 voltages in this case, which can be recorded at frame rates between 10 Hz and 50 Hz. The number of 208 measured voltages is obtained in a 16-electrode system if each of the 16 pairs of adjacent electrodes is used once as a feeding electrode pair, and there are 13 different pairs of adjacent electrodes, between which a measured voltage is detected, among the 14 remaining electrodes, so that a total of 16×13=208 measured voltages are detected during one run. This is a typical mode of actuation for an EIT device with a 16-electrode system. However, it is also conceivable in technical implementations of EIT devices that not all of the existing electrodes are used to feed current or voltage, but individual electrodes or electrode pairs are jumped over during the feed. It is likewise conceivable that voltage measurements or current measurements are not performed on all of the existing electrodes, but individual electrodes or electrode pairs are jumped over and omitted during the measurements.

The 208 time series of the voltages are transported in the present exemplary embodiment to the memory unit 7 of the EIT device or to an external memory unit via a bus system 6. The 1024 (relative) impedance changes $Z_1, Z_2, \ldots Z_{1024}$, which will be imaged on an image with 32×32 image elements, are reconstructed from the measured voltages. The reconstruction and further analyses may take place both online and offline, offset in time and space. The data generated subsequently can therefore be stored internally in the EIT system via a bus system or in an external memory. A distinction will no longer be made below between the two possibilities.

A computer module reconstructs the 1024 time series of the relative impedance changes $(Z_1(t), Z_2(t), Z_{1024}(t))$ from the 208 time series of the voltages $U_1(t), U_2(t), \ldots U_{208}(t)$ and makes them available in a local impedance module 8. Only the information-carrying "ventilated" image elements (pixels) $i=[1, 2, \ldots N_{pix}]$ are selected with a preset image element mask 9 or image element mask determined from the data, i.e., the marginal elements 9 indicated in FIG. 1 outside the lung are blanked out.

Figure 2:
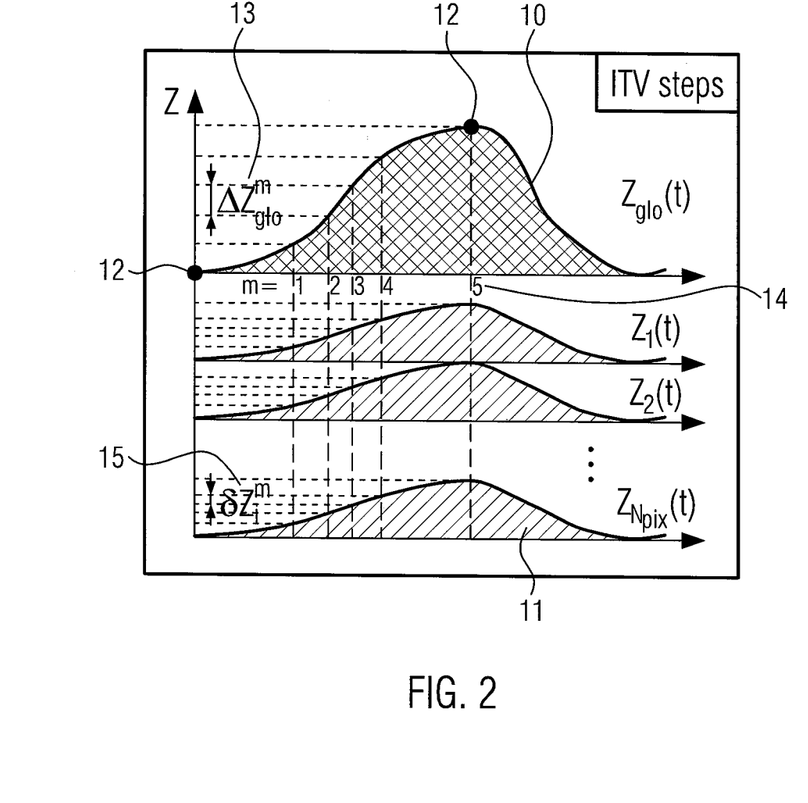
FIG. 2 is a schematic view of an analysis module of the control and analyzing unit of the electric impedance tomography device for explaining the functions thereof.

FIG. 2 schematically shows an analysis module of the control and analyzing unit. The top part of FIG. 2 schematically shows the global (relative) impedance change time series $Z_{glo}(t)$ 10, called global impedance curve for short, which is determined by adding up the local (relative) impedance change time series $Z_i(t)$ 11 and is optionally standardized in a suitable manner. This global impedance curve $Z_{glo}(t)$ represents the global impedance change as opposed to the local impedance change $Z_i(t)$ of the individual image elements. The global impedance change time series or impedance change curve is closely correlated with the ventilation volume curve based on the nearly complete proportionality between the breathing air volume change and the impedance change; in case of a respirator respirating the patient, the impedance change can also be standardized for the volume curve of the respirator.

Based on the close correlation of the global impedance change, which is shown in the top part of FIG. 2, with the volume curve of respiration, the global impedance curve $Z_{glo}(t)$ can be used to determine the inspiration phase and expiration phase, i.e., the beginning and the end of the inspiration flank and the beginning and the end of the expiration flank can be determined by the control and analyzing unit in the global impedance curve. FIG. 2 schematically shows the analysis module of the control and analyzing unit, in which module the global impedance curve $Z_{glo}(t)$ and the local impedance curves $Z_1(t), Z_2(t), \ldots, Z_{Kpix}(t)$ are recorded and analyzed. The inspiration phase is determined in the global impedance curve $Z_{glo}(t)$ and marked by the starting and end points 12.

The mean slope multiplied by the number of ITV steps $M_{steps}$ is selected as the scalar indicator (ITU value) of the ITV curves for the inspiration phase in the exemplary embodiment. Despite the reduction of the information of the points of the curve to one value only, this parameter reflects fundamental information: Which are the areas of the lungs that contain less of the inspired air at the beginning of inspiration and which are the lung areas that contain more of the inspired air at the end or vice versa and how great is the redistribution of the respirated partial air volumes during one breath. The representation of the image elements as a function of this parameter will hereinafter be called ITU map (intratidal redistribution map). Half of the sum of the values of the ITU map is selected as the global variable, because this represents a simple interpretation as a relative percentage of the redistributed quantity of the respirated partial air volumes.

The inspiration flank between the beginning and the end of inspiration of the global impedance curve is divided according to the ITV method described in EP 2 228 009 A1 (corresponding to U.S. Pat. No. 8,321,007, U.S. Pat. No. 8,321,007 is hereby incorporated by reference in its entirety) into $M_{steps}$ equidistant global impedance change steps $\Delta Z^m_{glo}$=const., m=1 ... $M_{steps}$, indicated in FIG. 2 by the horizontal dotted lines at 13, which are all equidistant, i.e., correspond to equal volume change steps or partial air volumes of inspiration. The number of steps is selected at $M_{steps}$=5 in FIG. 2. The step size $\Delta Z^m_{glo}$ can be considered to be the inspired partial air volume, and the division into $M_{steps}$ impedance change steps corresponds based on the close correlation of the impedance change curve with the volume curve to a division of the volume curve of the inspiration phase into $M_{steps}$ equal volume change steps $\Delta V$. The corresponding steps are not spaced apart, in general, equidistantly in the time range, which is indicated by the vertical dashed lines at the steps 1, 2, 3, 4 and 5 based on the generally non-constant flow dV/dt. The times that correspond to the same volume steps and are indicated in FIG. 2 by the vertical dashed lines are used as the times or support points to analyze the local impedance change curve and to set up the time series thereof. The analysis of the local impedance change curves according to equal volume change steps $\Delta V$ can be interpreted practically such that the local ventilation curve is plotted as a function of the global ventilation curve of 0, $\Delta V$, $2 \cdot \Delta V$, ... $M_{steps} \cdot \Delta V$.

The local impedance change $\delta Z_i^m$, which is standardized with the global impedance change $\Delta Z_{glo}^m$ for this step to the local ITV value $\zeta_i^m$, is used for each image element i and each step m:

$$\zeta_i^m = \frac{\delta Z_i^m}{\Delta Z_{glo}^m} \cdot 100,$$

wherein $$\sum_{i=1}^{N_{pix}} \zeta_i^m = 100\%$$

because of $$\sum_{i=1}^{N_{pix}} \zeta_i^m = \Delta Z_{glo}^m$$

for all steps m=1, . . . $M_{steps}$.

The slope $S_i$ of a straight line fitted to the $\zeta_i^m$ values is determined for each image element I for the m=1, . . . $M_{steps}$ ITV values by root mean square error minimization and multiplied by the number of ITV steps $M_{steps}$:

$$S_i = \frac{\sum_{m=1}^{M_{steps}} \zeta_i^m \sum_{m=1}^{M_{steps}} m - M_{steps} \sum_{m=1}^{M_{steps}} \zeta_i^m m}{\left(\sum_{m=1}^{M_{steps}} m\right)^2 - M_{steps} \sum_{m=1}^{M_{steps}} m^2} \cdot M_{steps}$$

The multiplication by the number of ITV steps $M_{steps}$ causes, on the one hand, independence of the values $S_i$ from the number of ITV steps aside from statistical variations and, on the other hand, a simple possibility of interpreting the variable as a mean local intratidal redistribution of the inspired partial inspiration volumes from the beginning to the end of inspiration (or of the expired partial air volumes over the expiration). This value $S_i$ is therefore called local or regional ITU value (intratidal redistribution value) 19.

For example, a local ITU value of $S_i$=1.5% thus means that the percentage of inspired air increased for this pixel, on average, by 1.5% during the inspiration from the beginning to the end. This consequently means that less air entered the region of the image element at the beginning than at the end, which may indicate a change in the local time constant of the compartment during the breath, and even tidal recruitment in the extreme case.

Local ITU values (for one image element) above 1% can already be classified as rather high. The local ITU values, which are in the given ROI, are added up for ITU values of larger regions (ROIs). A ROI (Region of Interest), which contains, e.g., 50 image elements of an image element mask of an EIT image with 32×32 image elements, which said masks comprises, e.g., 300 image elements, would now have a regional ITU value greater than 50% if the individual image elements had local ITU values of 1%. This means that only 50% of the inspired partial air volumes are redistributed in this ROI, i.e., that this region contains 50% more (or less) of the inspired partial air volume, e.g., at the end than at the beginning, which would indicate tidal recruitment or total hyperdistension or mutually greatly differing time constants in this region of the lung in different areas of the lungs because of, e.g., COPD.

Figure 3:
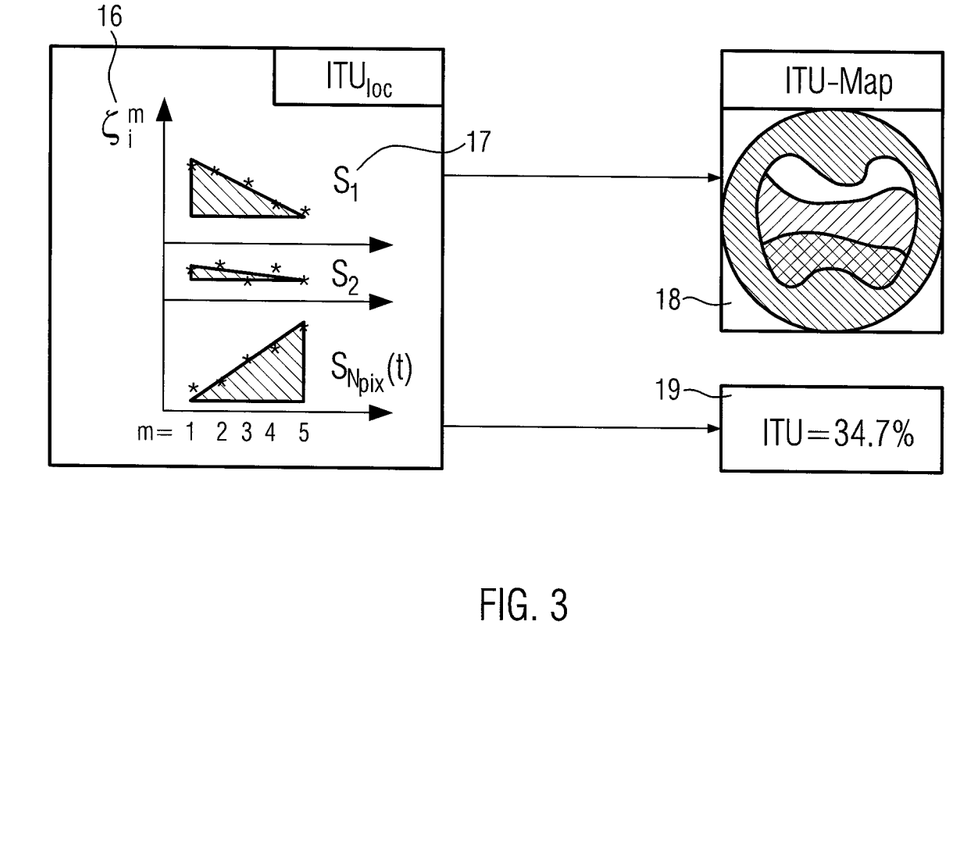
FIG. 3 is a schematic view of components or modules and display means of the electric impedance tomography device for explaining the functions thereof.

The ITU values $S_i$, I=1 . . . $N_{pix}$ are displayed by means of color coding as an image (ITU map) of the same size as the image with 32×32 image elements, as this is schematically indicated in the display means 18 in FIG. 3.

Based on the above definition of $\zeta_i^m$, $$\sum_{i=1}^{N_{pix}} \left( \sum_{m=1}^{M_{steps}} \zeta_i^m \sum_{m=1}^{M_{steps}} m - M_{steps} \sum_{m=1}^{M_{steps}} \zeta_i^m m \right) =$$

$$\sum_{m=1}^{M_{steps}} m \sum_{m=1}^{M_{steps}} \sum_{i}^{N_{pix}} \zeta_i^m - M_{steps} \sum_{m=1}^{M_{steps}} m \sum_{i=1}^{N_{pix}} \zeta_i^m =$$

$$\left( \sum_{m=1}^{M_{steps}} m \right) \cdot M_{steps} \cdot 100 - M_{steps} \left( \sum_{m=1}^{M_{steps}} m \right) \cdot 100 = 0$$

and thus $$\sum_{i=1}^{N_{pix}} S_i = 0$$

follows, which is also vividly clear, because if a relatively large percentage of the (constant) partial air volume being inspired enters a lung area, a lower percentage of the partial air volume must inherently enter another lung area if the total sum is constant, namely, $\Delta V$.

Therefore, half of the sum of the values is defined as the global ITU value or ITU for short:

$$ITU = \frac{\sum_{i=1}^{N_{pix}} |S_i|}{2},$$

$$[ITU] = \%$$

This value is the relative intratidal redistribution of the partial air volumes being inspired from the beginning to the end of inspiration (or expiration). The range of values is between 0%≤ITU≤100%. The lower limit indicates fully homogeneous ventilation over time (not necessary in space), which means that equal time constants are present everywhere in the lung. This means the different ventilated regions of the lungs always receive an equal percentage of the ventilated partial air volume during each phase during inspiration (expiration). The upper limit indicates maximum redistribution. This means that all the air enters one area of the lung at the beginning of inspiration and the other area receives nothing, and all the air enters the other area at the end and the first one receives nothing: The ventilated (differential) partial air volumes are consequently completely redistributed regionally during the inspiration (expiration).

Autoscaling of the ITU map is not advisable, because images with low local ITU values of about $S_i$<0.1% would be represented as being the same as ITU maps with high local ITU values of $S_i$>1.0%. It is therefore advisable to define a common lower range of a minimal scaling. This requires examination of patients and test subjects in order to specify the valve range of the ITU values more closely. Empirical examinations showed that local ITU values of $S_i>0.75\%$ are already very high and rare, so that it can be recommended that a common lower ITU map scale in a range of about $-0.75\%<S_i<+0.75\%$ (or higher) be used.

Figure 4:
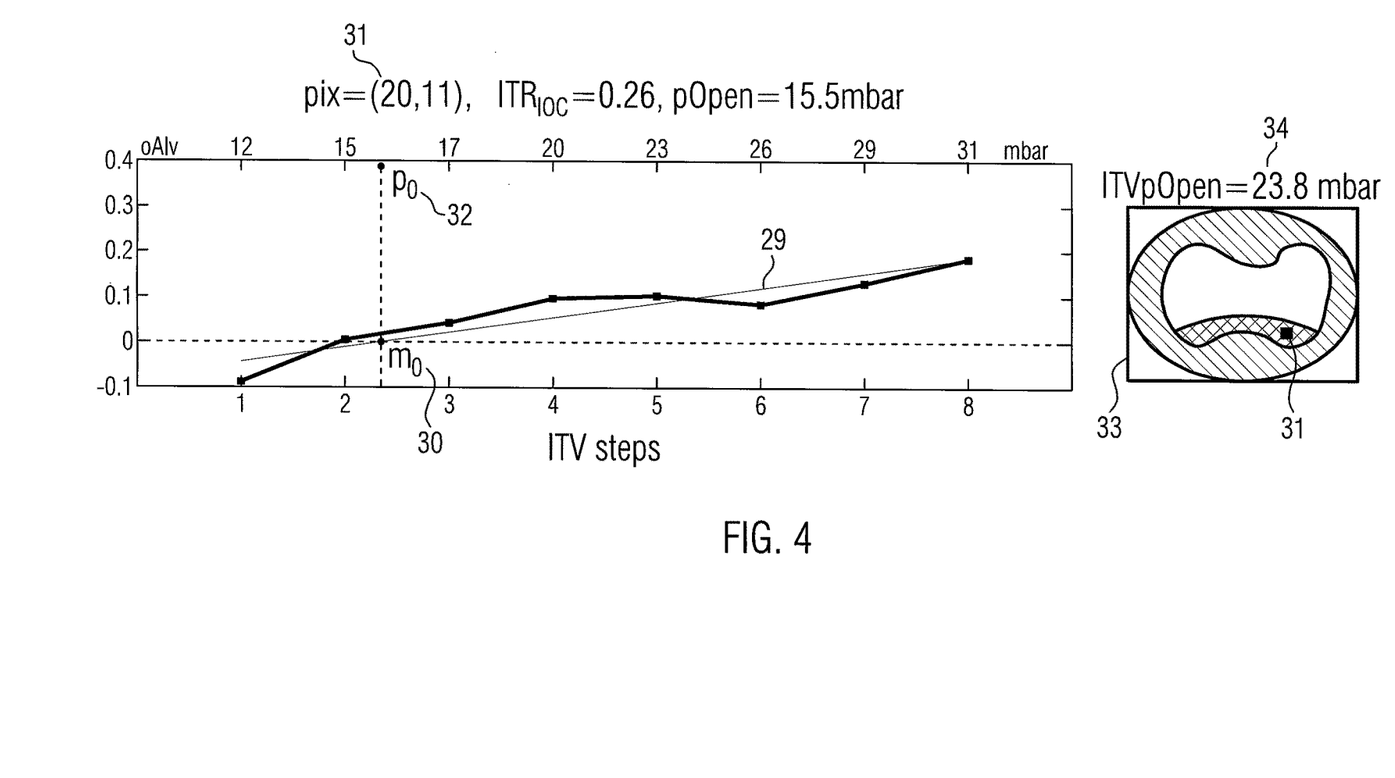
FIG. 4 is a view showing the local impedance change relative to the volume step of an image element as a function of the step number of a preset number of equal volume steps.

Another variable, which is of interest for respiration, can be derived from the local $S_i$ values, on which the ITU map is based. The $\zeta_i^m$ graph of the first, second and N-th image element is shown as an example in FIG. 3. When examining the lowermost of the three $\zeta_i^m$ graphs in box 16 in FIG. 3, it is found that the curve fitted to the data is rising. Since a fit of a straight line is used in this exemplary embodiment as a fit, this is a positive slope (S/M$_{step}$). This is illustrated in FIG. 4 for a real data set from the example of a case. Reference will hereinafter be made to FIG. 4.

The zero position $m_1^0$ 30 of image element I=(20,11)= 20*32+11=651, which is designated by 31, is determined from the fitted straight line 29. The respiration pressure curves were present in this data set. The alveolar pressure curve was determined from the respiration pressure curve by means of a one-compartment model, which takes into account the pressure drops due to turbulences at the mouthpiece and due to friction in the upper airways. An alveolar pressure for the lung area of image element I=(20,11) of $p_i^0=15.5$ bar corresponds to the zero position $m_i^0=2.3$. This pressure can be interpreted as the opening pressure in this lung region in connection with the known lung damage in the case of this example and will also be called such below. The method is performed for all pixels with positive ITU values, and meaningless opening pressure values $p_i^0<0$ will be set to 0. If the zero crossing takes place within the tidal stroke as in this example (min($p_{alv}$)=12 bar<$p_i^0$=15.5 mbar<max ($p_{alv}$)=31 mbar), this strongly indicates tidal recruitment, i.e., that the alveoli cyclically open during inspiration and collapse again at the end of expiration, a process that leads to destruction of the alveoli because of strong tension forces and must be avoided. This case can also be determined without the existence of information on pressure because this requires only a zero position in the range of $1<m_i^0<M_{steps}$. The corresponding information on alveolar pressure, which may possibly be available, indicates the PEEP beginning from which the alveoli remain open.

If the zero position is $m_i^0<1$, i.e., it is located before the beginning of the tidal stroke, a value $p_i^0>0$ may still always exist at PEEP values>0 (PEEP: Positive End Expiratory Pressure) by extrapolating the functional relationship between the ITV steps m and the corresponding alveolar pressures $p_{alv}$(m). There probably is no tidal recruitment in this case, but the value of the opening pressure does indicate the PEEP values lower than those being used beginning from which the corresponding lung areas would possibly collapse.

The opening pressures pi0, I=1 ... 1024, determined pixel by pixel, can be displayed coded as an opening pressure image 33. A global opening pressure value 34 is determined, here from the mean value of the upper quantile, from the opening pressure image from the $p_i^0$ values that are greater than 0.

While specific embodiments of the invention have been shown and described in detail to illustrate the application of the principles of the invention, it will be understood that the invention may be embodied otherwise without departing from such principles.

What is claimed is:

1. An electric impedance tomography device comprising:
a display device; and
a control and analyzing unit receiving a sequence of matrices of impedance change values, wherein the matrices each represent a distribution of impedance changes in an electrode plane, with each impedance change value having a position in a matrix corresponding to an image element position wherein the control and analyzing unit;
determines a time series of the impedance change values, as a global ventilation curve: from the sequence of matrices of impedance change values as a time series of mean impedance changes or as a time series of a measured respiration volume, and determines an inspiration or expiration phase of the global ventilation curve,
divides the inspiration or expiration phase of the global ventilation curve into a number of steps of equal volume change,
determines times corresponding to these steps of equal volume change in the determined inspiration or expiration phase,
determines a change in the impedance change values between the times corresponding to the steps of equal volume change for each image element position,
determines for each of the times, corresponding to the steps of equal volume change, a ratio of said change in the impedance change values of each the image element position to said global ventilation curve to form a local sequence of relative impedance changes of the image element position as a function of the number of steps of equal volume change, indicative of an intratidal distribution value (ITV) of the image element position,
determines, for each said local sequence of relative impedance changes of the image element position as a function of the number of steps of equal volume change, a scalar indicator, which is indicative, for the number of steps of equal volume change, of the ITV
displays image elements on the display device such that each of the image elements has a visual gray scale value or a color coding value on the display device that depends on one particular scalar indicator of the local sequence of relative impedance changes of the image element position.

2. An electric impedance tomography device in accordance with claim 1, wherein the control and analyzing unit is configured to determine as the scalar indicator of a local sequence of the relative impedance changes as a function of the steps of equal volume change of an image element position; a mean slope of a local sequence of the relative impedance changes as a function of the steps of equal volume change of an image element over the inspiration or expiration phase, multiplied by a constant; a standard deviation thereof; a maxima of the values of local slopes within the inspiration or expiration phase; or a maximum change in slope within the inspiration or expiration phase.

3. An electric impedance tomography device in accordance with claim 1, wherein the control and analyzing unit is configured to fit a straight line to the local sequence of the relative impedance changes as a function of the step number of the equal volume changes during an inspiration or expiration phase for each image element position and determine a zero position thereof, to assign to this zero position a time within the inspiration or expiration phase and to assign based on this a ventilation variable to this time and to display the image element as a function of the ventilation variable thus determined in gray scale value or color coding on the display device.

4. An electric impedance tomography device in accordance with claim 3, wherein the control and analyzing unit is configured to use, as the ventilation variable, the global time series of the impedance change, volume, flow or respiration pressure from a respirator or alveolar pressure calculated from these variables by means of a model.

5. An electric impedance tomography device in accordance with claim 1, wherein the control and analyzing unit is configured to perform the determination of the time series and of the scalar indicator of a local time series for each image element position in real time.

6. An electric impedance tomography device in accordance with claim 1, wherein the control and analyzing unit is configured to store the measured signals and to perform the determination of the time series and of the scalar indicator of a local time series for each image element position with a time delay.

7. An electric impedance tomography device in accordance with claim 1, wherein the control and analyzing unit is configured to convert the scalar indicators for a local time series into a color code and to display the image element in a color-coded form on the display device.

8. An electric impedance tomography device in accordance with claim 2, wherein the control and analyzing unit is configured to combine the scalar indicators for the local sequence of relative impedance changes in the image element positions into a global parameter and to display the global parameter alphanumerically and/or graphically on the display device, wherein the sum of all positive or negative slopes or the halved sum of the values of the slopes is used as the global parameter if the mean slope, multiplied by a constant, is used as the scalar indicator; the standard deviation added up over all image elements or the averaged standard deviation is used as the global parameter if the standard deviation is used as the scalar indicator; the sum of all maxima of the local slopes, multiplied by a constant, is used if the maxima of the local slopes are used as the scalar indicator; and the sum of all maximum slope changes, multiplied by a constant, is used as the global parameter if the maximum slope change, multiplied by a constant, is used as the scalar indicator.

9. A method for recording a sequence of EIT images of a cross-sectional plane of the chest of a patient by a plurality of electrodes distributed over the circumference of the chest, the method comprising the steps of:

providing a control and analyzing unit connected to a display device, with the control and analyzing unit:

receiving a sequence of matrices of impedance change values with each matrix of the matrices representing a distribution of impedance changes in an electrode plane, with each impedance change value having a position in the matrix corresponding to an image element position;

determining a time series of the impedance change values, as a global ventilation curve, from the sequence of matrices of impedance change values, as a time series of mean impedance changes or as a time series of a measured respiration volume;

determining an inspiration or expiration phase of the global ventilation curve;

dividing the inspiration or expiration phase of the global ventilation curve into a number of steps of equal global volume change, determining times corresponding to the steps of equal volume change in the inspiration or expiration phase;

determining a change in the impedance change values between the times corresponding to the steps of equal volume change, for each image element position;

forming, at the determined times of equal volume change, a ratio of the change in the impedance change values of each image element position to the global ventilation curve to form a sequence of local relative impedance changes of the image element position as a function of the steps of equal volume change, indicative of an intratidal distribution value (ITV) of the image element position;

determining, for each sequence of local relative impedance changes as a function of the steps of equal volume change, a scalar indicator, which is indicative of the ITV for the number of steps of equal volume change for each image element position; and displaying image elements, on the display device such that each of the image elements has a visual gray scale value or a color coding value on the display device that depends on one, particular scalar indicator of the local sequence of relative impedance changes of the image element position.

10. A method in accordance with claim 9, wherein the control and analyzing unit is configured to determine as the scalar indicator of a local sequence of the relative impedance changes as a function of the steps of equal volume change of an image element position; a mean slope of a local sequence of the relative impedance changes as a function of the steps of equal volume change of an image element, over the inspiration or expiration phase; a standard deviation of a local sequence of the relative impedance changes as a function of the steps of equal volume change of an image element position; a maxima of the values of local slopes within the inspiration or expiration phase; or a maximum change in slope within the inspiration or expiration phase.

11. A method in accordance with claim 9, wherein the control and analyzing unit is configured to fit a straight line to the local sequence of the relative impedance changes as a function of the step number of the equal volume changes during an inspiration or expiration phase for each image element position and determine a zero position thereof, to assign to the zero position a time within the inspiration or expiration phase, and to assign a ventilation variable to the time, and to display the image element as a function of the ventilation variable thus determined in gray scale value or color coding on the display device.

12. A method in accordance with claim 11, wherein the control and analyzing unit is configured to use, as the ventilation variable, the global time series of the impedance change, volume, flow or respiration pressure from a respirator or alveolar pressure calculated from these variables by means of a model.

13. A method in accordance with claim 9, wherein the control and analyzing unit is configured to display each image element position, beginning from the second of the number of times determined for the determined times of equal volume change steps as a function of the difference of the local impedance change of the image element and the local impedance change from the preceding time by gray scale value or color coding on the display device.

14. A method in accordance with claim 9, wherein the control and analyzing unit is configured to convert the scalar indicators for a local time series into a color code and to display the image element in a color-coded form on the display device.

15. An electric impedance tomography device in accordance with claim 9, wherein the control and analyzing unit is configured to combine the scalar indicators for the local sequence of relative impedance changes in the image element positions into a global parameter and to display the global parameter alphanumerically and/or graphically on the display device, wherein the sum of all positive or negative slopes or the halved sum of the values of the slopes is used as the global parameter if the mean slope is used as the scalar indicator; the standard deviation added up over all image elements or the averaged standard deviation is used as the global parameter if the standard deviation is used as the scalar indicator; the sum of all maxima of the local slopes is used if the maxima of the local slopes are used as the scalar indicator; and the sum of all maximum slope changes is used as the global parameter if the maximum slope change is used as the scalar indicator.

16. An electric impedance tomography system comprising:
- a display device; and
- a control and analyzing unit configured to receive a sequence of matrices, each matrix of the matrices comprising a distribution of impedance changes values with each impedance change value having a position in the matrix corresponding to an image element position;
- determine a time series of a global ventilation curve, from the sequence of matrices, as a time series of mean impedance changes or as a time series of a measured respiration volume;
- determine an inspiration or expiration phase of the global ventilation curve;
- divide the inspiration or expiration phase of the global ventilation curve into a number of steps of equal global volume change;
- determine times corresponding to the steps of equal volume change in the inspiration or expiration phase;
- form, at the determined times of equal volume change, a ratio of a change in the impedance changes to the global ventilation curve for each image element position, and form a sequence of the local relative impedance changes as a function of the steps of equal global volume change, indicative of an intratidal distribution value (ITV) of the image element position;
- determine a scalar indicator characteristic of the sequence of the local relative impedance change for each image element position, which is indicative of the ITV for the number of steps of equal volume change for the image element position; and
- control a display of image elements, on the display device such that each of the image elements has a visual gray scale value or a color coding value on the display device that depends on one particular scalar indicator of the local sequence of relative impedance changes of the image element position.

17. An electric impedance tomography system in accordance with claim 16, wherein:
- to determine the scalar value the control and analyzing unit is configured to fit a straight line to the local sequence of the relative impedance changes as a function of the step number of the equal volume changes during an inspiration or expiration phase for each image element position and to determine a zero position thereof, to assign to the zero position a time within the inspiration or expiration phase, and to assign a ventilation variable to the time, and to display the image element as a function of the ventilation variable thus determined in gray scale value or color coding on the display device.

* * * * *